US012465663B2

(12) United States Patent
Hansson

(10) Patent No.: US 12,465,663 B2
(45) Date of Patent: Nov. 11, 2025

(54) SCREEN COVER DEVICE FOR AN AIR-CLEANING DEVICE

(71) Applicant: TOUL MEDITECH AB, Västerås (SE)

(72) Inventor: Tomas Hansson, Västerås (SE)

(73) Assignee: TOUL MEDITECH AB, Västerås (SE)

( * ) Notice: Subject to any disclaimer, the term of this patent is extended or adjusted under 35 U.S.C. 154(b) by 706 days.

(21) Appl. No.: 17/790,532

(22) PCT Filed: Dec. 18, 2020

(86) PCT No.: PCT/SE2020/051231
§ 371 (c)(1),
(2) Date: Jul. 1, 2022

(87) PCT Pub. No.: WO2021/141522
PCT Pub. Date: Jul. 15, 2021

(65) Prior Publication Data

US 2023/0036753 A1 Feb. 2, 2023

(30) Foreign Application Priority Data

Jan. 7, 2020 (SE) .................................... 2050006-2

(51) Int. Cl.
*A61L 9/20* (2006.01)

(52) U.S. Cl.
CPC ..................................... *A61L 9/20* (2013.01)

(58) Field of Classification Search
USPC .................................................... 250/455.11
See application file for complete search history.

(56) References Cited

U.S. PATENT DOCUMENTS 4,045,192 A 8/1977 Eckstein et al.
4,229,202 A * 10/1980 Mullerheim .............. C05F 7/00 210/764
5,369,892 A * 12/1994 Dhaemers ............... F26B 21/00 34/224

(Continued)

FOREIGN PATENT DOCUMENTS

CA 2977955 A1 2/2019
CN 2886398 Y 4/2007

(Continued)

OTHER PUBLICATIONS

Toul Meditech AB, European Patent Application No. 20912405.6, Extended European Search Report, Dec. 8, 2023.

(Continued)

*Primary Examiner* — Kiet T Nguyen
(74) *Attorney, Agent, or Firm* — Moore & Van Allen PLLC; W. Kevin Ransom

(57) ABSTRACT

A screen cover device and an air-cleaning device configured to be used together with such a screen cover device, wherein said screen cover device is configured for holding at least one disposable screen cover which when in use, is configured for covering at least a substantial part of an air outflow area of a screen of the air-cleaning device, wherein said screen cover device is provided as an attachment to the air-cleaning device and comprises: at least one disposable screen cover; and a first unit which is configured for keeping the at least one disposable screen cover when not in use and which is configured to be mounted to the air-cleaning device.

17 Claims, 4 Drawing Sheets

(56) References Cited

U.S. PATENT DOCUMENTS

| | | | | |
|---|---|---|---|---|
| 6,680,028 | B1 * | 1/2004 | Harris | F24F 1/0071 96/132 |
| 6,811,593 | B2 | 11/2004 | Hansson et al. | |
| 2008/0194009 | A1 * | 8/2008 | Marentis | A61L 9/16 435/283.1 |
| 2008/0216844 | A1 | 9/2008 | Olfert et al. | |
| 2009/0233540 | A1 | 9/2009 | Valentino | |
| 2011/0005178 | A1 | 1/2011 | Lyons et al. | |
| 2013/0263868 | A1 | 10/2013 | Grenier | |

FOREIGN PATENT DOCUMENTS

| | | | |
|---|---|---|---|
| CN | 106309074 | A | 1/2017 |
| EP | 1958568 | A1 | 8/2008 |
| JP | 04250808 | A | 9/1992 |
| KR | 101963804 | B1 | 3/2019 |
| WO | 2018201186 | A1 | 11/2018 |

OTHER PUBLICATIONS

Toul Meditech AB, International Patent Application No. PCT/SE2020/051231, International Preliminary Report on Patentability, Jul. 12, 2022.

Toul Meditech AB, International Patent Application No. PCT/SE2020/051231, International Search Report, Feb. 11, 2021.

Toul Meditech AB, International Patent Application No. PCT/SE2020/051231, Written Opinion, Feb. 11, 2021.

* cited by examiner

SCREEN COVER DEVICE FOR AN AIR-CLEANING DEVICE

CROSS-REFERENCE TO RELATED APPLICATIONS

This application is a National Stage Patent Application (filed under 35 § U.S.C. 371) of PCT/SE2020/051231, filed Dec. 18, 2020, of the same title, which, in turn claims priority to Swedish Patent Application No. 2050006-2 filed Jan. 7, 2020, of the same title; the contents of each of which are hereby incorporated by reference.

FIELD OF THE INVENTION

The present invention relates to screen covers for an air-cleaning device. It furthermore relates to an air-cleaning device.

BACKGROUND OF THE INVENTION

Air-cleaning devices are useful in sensitive environments such as for example operating rooms, drug manufacture, micro-chip production and similar areas. Movable air-cleaning devices are for example described in U.S. Pat. No. 6,811,593. Such air-cleaning devices can for example be positioned in front of an operating table or an instrument table for providing a clean air flow over the table. A single use screen cover is sometimes provided over a screen of the air-cleaning device. Hereby the risk that the staff working during the surgery will destroy their sterility by touching the air-cleaning device is reduced since touching the single-use screen cover would not be a problem. A single use screen cover may be provided for improving sterility and for providing a laminar air flow.

SUMMARY OF THE INVENTION

An object of the invention is to provide improved disposable screen covers for air-cleaning devices.

A further object of the invention is to provide user-friendly screen covers.

This is achieved by a screen cover device, an air-cleaning device and an air-cleaning device system according to the independent claims.

According to one aspect of the invention a screen cover device is provided for holding at least one disposable screen cover which when in use is configured for covering at least a substantial part of an air outflow area of a screen of an air-cleaning device, wherein said screen cover device is provided as an attachment to the air-cleaning device and comprises:

at least one disposable screen cover; and a first unit which is configured for keeping the at least one disposable screen cover when unused and which is configured to be mounted to the air-cleaning device.

According to another aspect of the invention an air-cleaning device is provided configured to be used together with a screen cover device as defined above, wherein said air-cleaning device comprises:

a screen with an air outflow area where clean air is flowed out from the air-cleaning device; and a first screen cover device holder for holding said first unit.

According to another aspect of the invention an air-cleaning device system comprising an air-cleaning device as described above and a screen cover device as described above is provided.

Hereby a screen cover device is provided which comprises at least one disposable screen cover. If more than one disposable screen covers are provided in the screen cover device they can be provided to the air-cleaning device one after the other, i.e. a new one for each use. Hereby a user-friendly device is provided which can be attached to an air-cleaning device. Hereby sterility in for example an operation room, a surgery preparation room, another type of health care room or another room where sterility is needed can be improved.

In some embodiments of the invention said screen cover device comprises at least two disposable screen covers which are in connection with each other such that they can be removed from the first unit one after each other.

In one embodiment of the invention the first unit comprises a roll around which the at least one unused disposable screen cover is rolled.

In one embodiment of the invention a first end of each disposable screen cover is configured for being connected to the air-cleaning device, whereby a second end of the disposable screen cover is held by the first unit when this disposable screen cover is the one presently in use covering an air outflow area of a screen of the air-cleaning device, which second end is opposite said first end of the disposable screen cover.

In one embodiment of the invention the screen cover device further comprises:

a second unit for collecting used disposable screen covers, which second unit is configured to be mounted to the air-cleaning device such that a screen cover which is the one presently in use for covering at least a substantial part of an air outflow area of a screen of the air-cleaning device is held between the first and the second units.

In one embodiment of the invention the second unit comprises a roll around which the used disposable screen covers are rolled.

In one embodiment of the invention the rolls of the first and second units are configured such that they can be rotated in coordination for unwinding unused disposable screen covers from the roll of the first unit and winding used disposable screen covers onto the roll of the second unit.

In one embodiment of the invention the disposable screen covers are designed to cover at least a substantial part of the air outflow area of the screen of the air-cleaning device and at least parts of side edges of the air-cleaning device and wherein the screen cover device is configured to be mounted to the air-cleaning device such that one of the disposable screen covers which is the one to be presently in use covers both at least a substantial part of the air outflow area of the screen of the air-cleaning device and at least parts of side edges of the air-cleaning device.

In one embodiment of the invention at least one of the disposable screen covers comprises a peelable protective layer.

In one embodiment of the invention the screen cover device is presterilized.

In one embodiment of the invention the air-cleaning device further comprises a second screen cover device holder for holding a second unit of a screen cover device or for holding a first end of a screen cover.

In one embodiment of the invention said second screen cover device holder is positioned such that a screen cover can be held in a first end either by a second unit or by the second screen cover device holder and in a second end by the first unit while the screen cover is covering at least a substantial part of the air outflow area of the screen of the air-cleaning device.

In one embodiment of the invention the air-cleaning device further comprises a germicidal radiation source positioned such that the disposable screen cover to be used can be irradiated.

In one embodiment of the invention said germicidal radiation source is provided such that it can irradiate the disposable screen cover which presently is in use and the air outflow from the air-cleaning device.

In one embodiment of the invention the air-cleaning device further comprises a frame configured to hold the one of the disposable screen covers which is the one to be presently in use in a position such that the disposable screen cover covers at least a substantial part of the air outflow area of the screen of the air-cleaning device.

In one embodiment of the invention the frame comprises guides which are bent such that the screen cover which is the one presently used is stretched over the guides and provides a curved surface of the screen cover.

DETAILED DESCRIPTION OF THE EMBODIMENTS

Figure 1A:
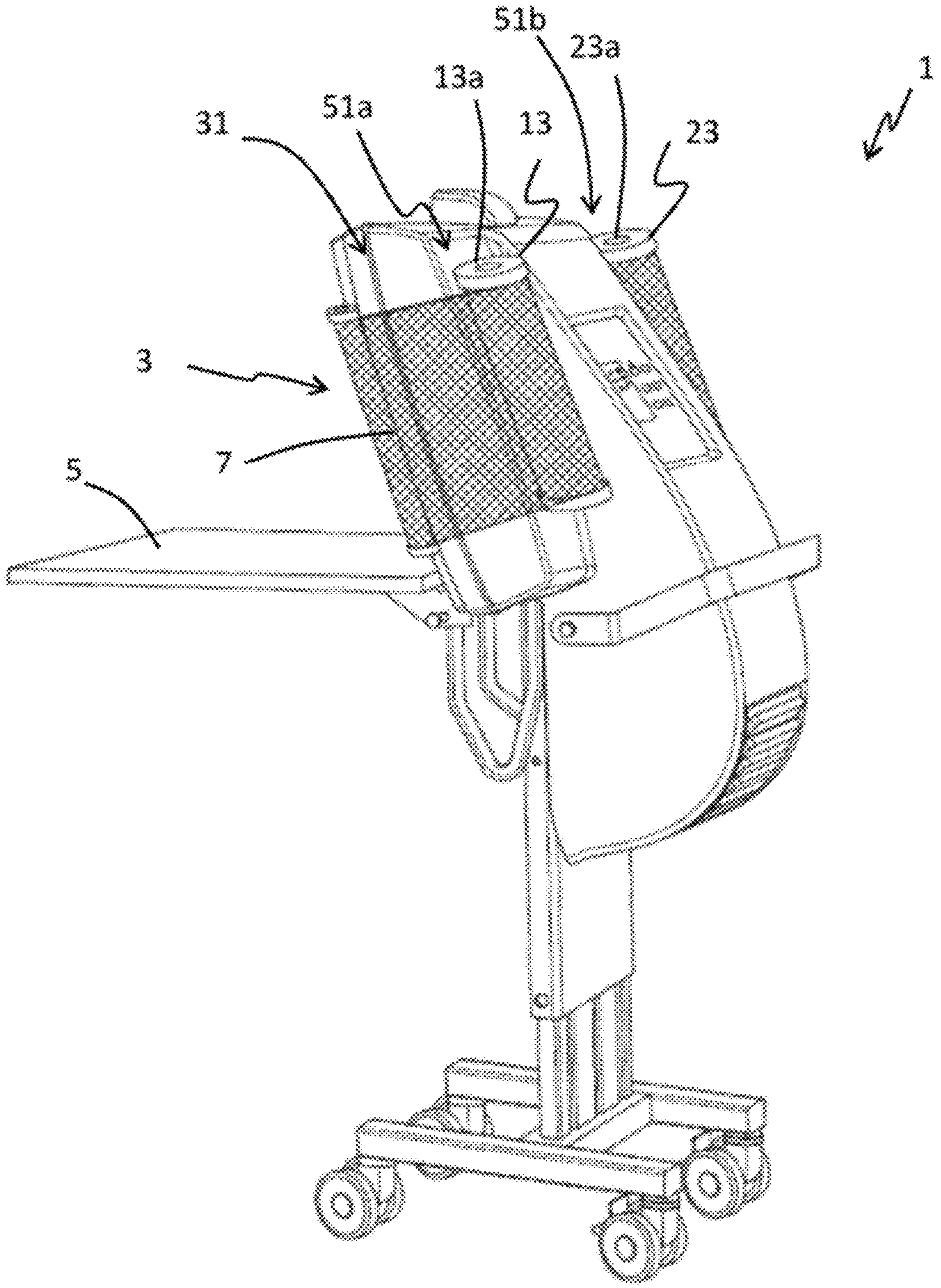
FIGS. 1*a* and 1*b* are two different perspective views of an air-cleaning device provided with a screen cover device according to one embodiment of the invention.
Figure 1B:
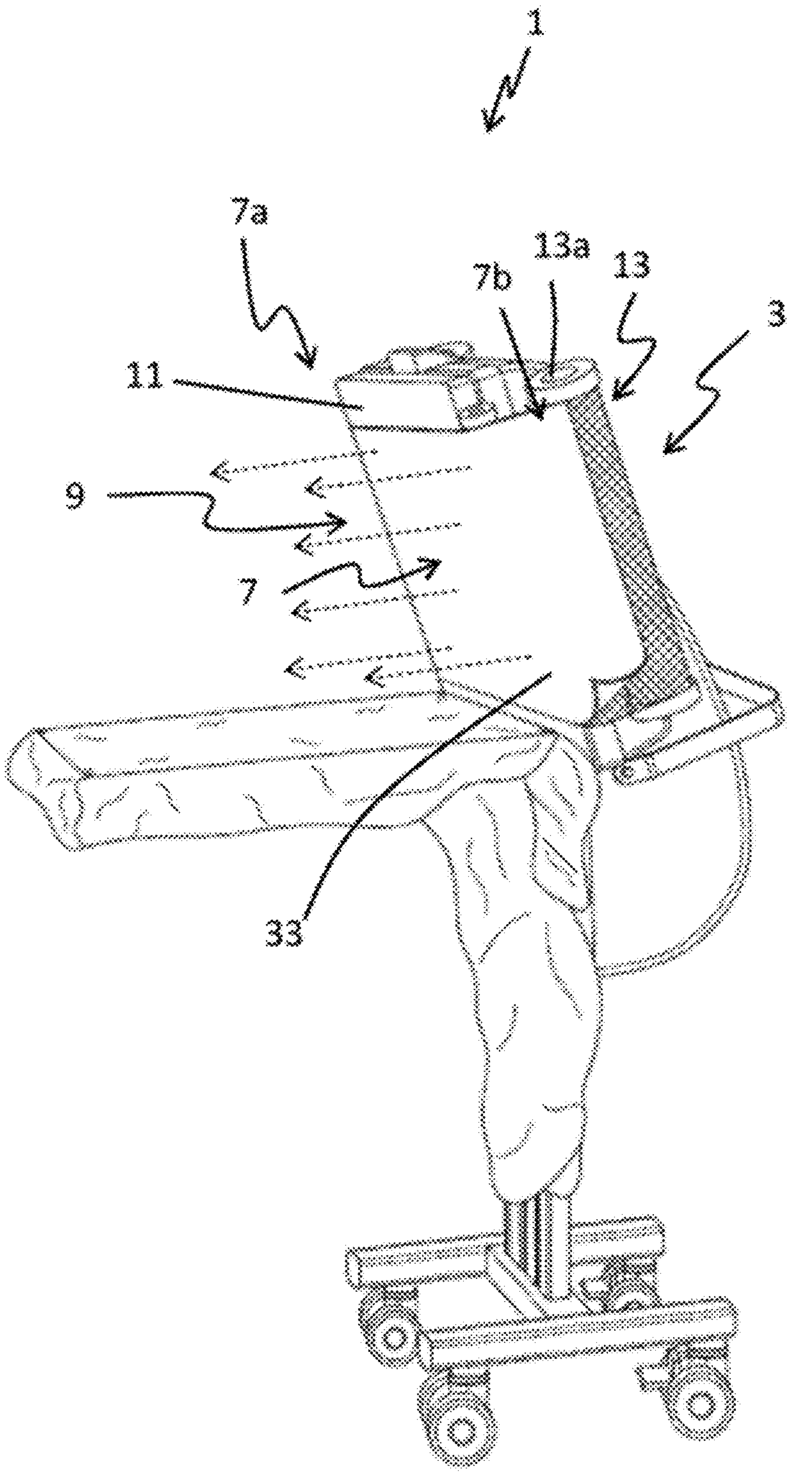
Figure 2:
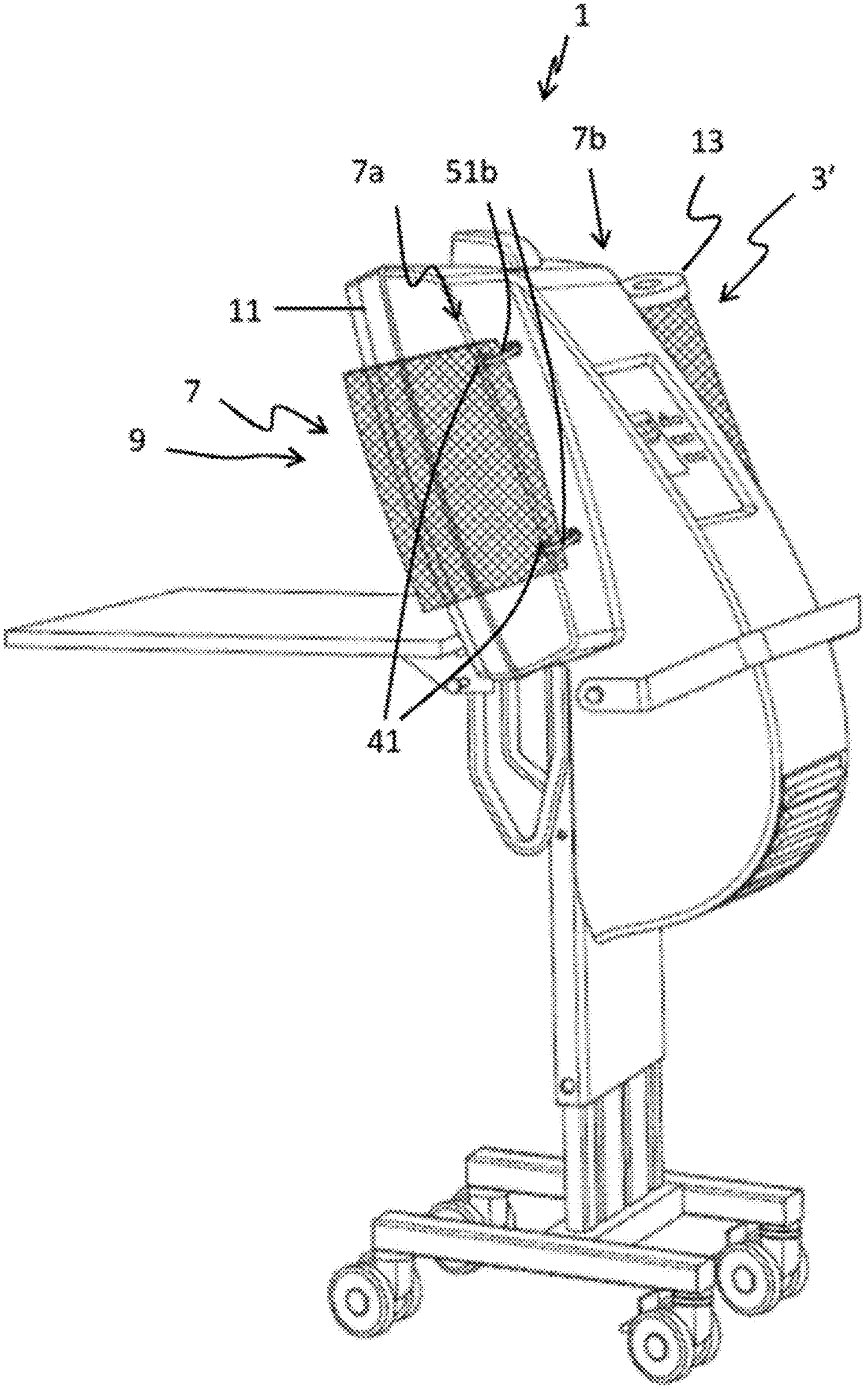
FIG. 2 shows an air-cleaning device provided with a screen cover device according to another embodiment of the invention.

FIGS. 1*a* and 1*b* are two different perspective views of an air-cleaning device 1 provided with a screen cover device 3 according to one embodiment of the invention. FIG. 2 shows an air-cleaning device 1 provided with a screen cover device 3' according to another embodiment of the invention and FIG. 3 is a perspective view from above of an air-cleaning device 1 provided with a screen cover device 3" according to still another embodiment of the invention.

Some of the details in these three different embodiments are the same or similar and are also given the same reference numbers and will be described together with reference to all the drawings. The air-cleaning device 1 is in this illustration a movable air-cleaning device 1 which suitably can be used in operating rooms. The air-cleaning device is here provided with a table 5 which can be fixed, foldable or removable. However, the air-cleaning device used in this invention does not need to have a table but can instead be positioned in front of an operating table or an instrument table for providing a clean air flow over the table. The air-cleaning device as used in this invention does not have to be movable but can instead be mounted to for example an operating table or an instrument table. It can instead also be provided to a wall mounted or ceiling mounted adjustable stand or frame allowing the air-cleaning device to be moved into different positions within a room.

According to the invention a screen cover device 3 is provided for holding at least one disposable screen covers 7 or a number of disposable screen covers 7 which when in use are configured for covering at least a substantial part of an air outflow area 9 of a screen 11 of the air-cleaning device 1. A substantial part of the air outflow area 9 would mean for example more than 75% of the air outflow area 9 or more than 90% of the air outflow area. According to the invention said screen cover device 3 is provided as an attachment to the air-cleaning device 1 and comprises a first unit 13 which is configured for holding at least one unused disposable screen cover 7 and which is configured to be mounted to the air-cleaning device 1. The one or more disposable screen covers 7 are before use kept or stored within the first unit 13 and the screen cover device 3 is configured for holding the disposable screen cover 7 which is presently in use for covering at least a substantial part of an air outflow area 9 of a screen 11 of an air-cleaning device. The disposable screen covers 7 provided in the screen cover device 3 are used one after each other for covering at least a substantial part of an air outflow area 9 of a screen 11 of an air-cleaning device. The screen cover device 3 comprises at least one disposable screen cover 7. With reference to FIG. 3, the screen cover device 3 comprises suitably at least two disposable screen covers 7, 7' which are in connection with each other such that they can be removed from the first unit 13 one after each other.

Figure 3:
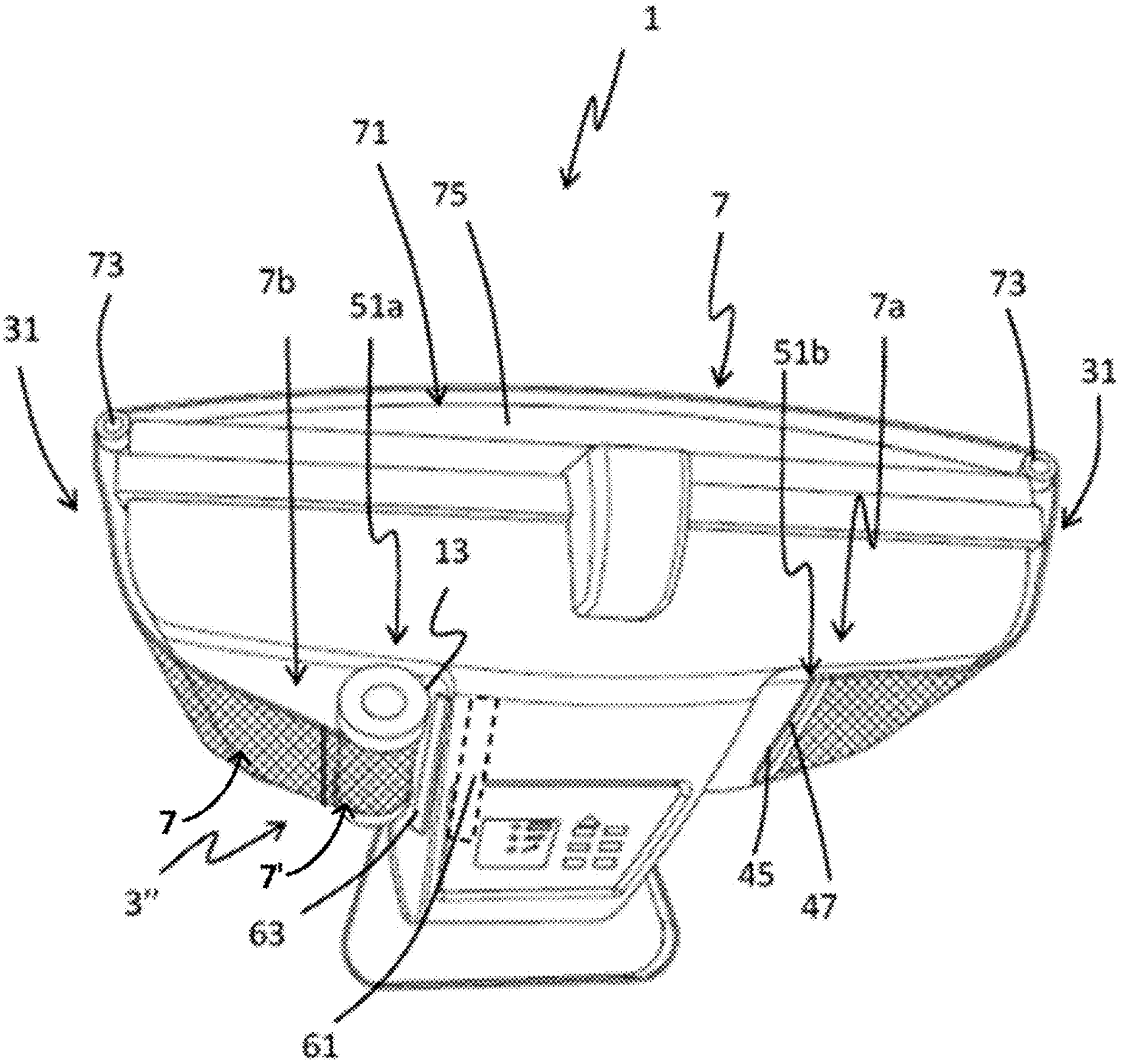
FIG. 3 is a perspective view from above of an air-cleaning device provided with a screen cover device according to another embodiment of the invention.

In all the embodiments as shown in FIGS. 1-3 the first unit 13 comprises a roll 13*a* around which the at least one unused disposable screen cover 7 is rolled. However, other alternatives than rolling the screen covers 7 around a roll are possible within the scope of the invention. For example, the first unit could instead be a cassette within which the screen covers 7 are folded.

In the embodiment of the invention as shown in FIGS. 1*a* and 1*b* the screen cover device 3 further comprises a second unit 23 for collecting used disposable screen covers 7, which second unit 23 is configured to be mounted to the air-cleaning device 1 such that a screen cover 7 which is the one presently in use for covering at least a substantial part of an air outflow area 9 of a screen 11 of the air-cleaning device 1 is held between the first unit 13 and the second unit 23. In this embodiment the second unit 23 comprises a roll 23*a* around which the used disposable screen covers 7 are rolled. However, in another embodiment the second unit 23 could as well be another type of cassette in which used screen covers 7 can be collected also in other ways than rolling them.

In a screen cover device 3 according to the embodiment as shown in FIGS. 1*a* and 1*b* the rolls 13*a*, 23*a* of the first and second units 13, 23 can be configured such that they can be rotated in coordination for unwinding unused disposable screen covers 7 from the roll 13*a* of the first unit 13 and winding used disposable screen covers 7 onto the roll 23*a* of the second unit 23. This can be done both manually by rotating one of the rolls 13*a*, 23*a* or powered by a motor. Hereby a new disposable screen cover 7 can easily be provided for, for example each new operation. The whole screen cover device 3 with its unused screen covers 7 may have been pre-sterilized before mounting to the air-cleaning device 1 and maybe even before delivery and packed in a sterile package for assuring a sterile product. The disposable screen covers 7 provided within the screen cover device 3 may also be provided with one or more protection films provided between each of the screen covers 7 for covering a connection boundary between the screen covers and possibly an area around the connection boundary. This protection film should protect the next following screen cover from a previous already used screen cover 7 and the protection film should not be removed until the previous screen cover 7 has been collected safely according to sterile routines. Hereby a risk for contamination from a previous operation can be avoided.

In the embodiments shown in FIG. 2 and FIG. 3 the screen cover device 3'; 3" does not comprise a second unit. Instead a first end 7*a* of each disposable screen cover 7 is configured for being connected to the air-cleaning device 1, whereby a second end 7*b* of the disposable screen cover 7 is held by the first unit 13 when this disposable screen cover 7 is the one presently in use covering an air outflow area 9 of a screen 11 of the air-cleaning device 1, which second end 7*b* is opposite said first end 7*a* of the disposable screen cover 7. The first end 7*a* of each disposable screen cover 7 comprises in some embodiments of the invention an air-cleaning device connector 41 for connection to a second screen cover device holder 51*b* provided on the air-cleaning device 1. A first screen cover device holder 51*b* is provided on an opposite side of the air-cleaning device 1 and is configured for holding the first unit 13 of the screen cover device 3; 3'; 3" which will be described further below. In the example as shown in FIG. 2 the air-cleaning device connector 41 comprises a number of openings and the second screen cover device holder 51*b* comprises a corresponding number of hooks. Alternatively, the air-cleaning device connector 41 can comprise for example a magnet, tape, adhesive or Velcro for connection to a corresponding second screen cover device holder 51*b*. However, if the air-cleaning device connector 41 is tape or adhesive it may not be necessary that the air-cleaning device 1 comprises a second screen cover device holder 51*b*. The air-cleaning device connector 41 can in that case be connected directly to any suitable surface of the air-cleaning device 1.

Another alternative is shown in FIG. 3 where a first end 7*a* of a disposable screen cover 7 is received in a second screen cover device holder 51*b*', wherein said second screen cover device holder 51*b*' comprises a groove 45 provided in the air-cleaning device 1 and a locking member 47 which can be received into the groove 45 and lock the first end 7*a* of the screen cover 7 between the groove 45 and the locking member 47.

The disposable screen covers 7 are suitably designed to cover at least a substantial part of the air outflow area 9 of the screen 11 of the air-cleaning device 1 and suitably also at least parts of side edges 31 of the air-cleaning device 1. Hereby, by covering a larger part of the air-cleaning device with a sterile screen cover there is less risk that personnel working in the operation room will destroy their sterility by unintentional touching a non-sterile part of the air-cleaning device 1. The screen cover device 3; 3'; 3" is configured to be mounted to the air-cleaning device 1 such that one of the disposable screen covers 7 which is the one to be presently in use covers both at least a substantial part of the air outflow area 9 of the screen 11 of the air-cleaning device 1 and at least parts of side edges 31 of the air-cleaning device 1.

At least some of the disposable screen covers 7 comprise in some embodiments of the invention each a peelable protective layer 33 covering substantially the whole screen cover 7. Substantially the whole screen cover 7 would mean at least 90% of the area of the screen cover 7, but suitably the whole area of the screen cover is covered. In some embodiments the peelable protective layer 33 even projects a few mm outside the screen cover 7 in order to assure sterility. A peelable protective layer 33 is only shown in FIG. 1*b* but peelable protective layers 33 can be provided in all embodiments of the invention. Such a peelable protective layer 33 can suitably be peeled off and disposed just before an operation is started or instruments are prepared on its table. Hereby sterility can be secured. The peelable protective layers 33 may be provided to the disposable screen covers 7 by a suitable adhesive such that they can easily be peeled off without leaving adhesive material on the screen cover 7.

The invention further relates to an air-cleaning device 1 configured to be used together with a screen cover device 3; 3'; 3" as described above in relation to FIGS. 1-3. Said air-cleaning device 1 comprises a screen 11 with an air outflow area 9 where clean air is flowed out from the air-cleaning device 1 and a first screen cover device holder 51*a* for holding the first unit 13 of the screen cover device 3; 3'; 3". If the first unit 13 is a roll 13*a* as described for some embodiments above and the roll comprises a central opening the first screen cover device holder 51*a* can comprise for example a rod which can be received in the central opening of the roll 13*a*. The first screen cover device holder 51*a* can also comprise an enclosing cassette attached to the air-cleaning device 1, into which cassette the first unit 13 can be pushed and whereby the screen covers 7 can be pulled out from the cassette through an opening. Such an enclosing cassette may be suitable when UV sterilization of the screen covers 7 is provided which will be further described below in relation to FIG. 3. The first screen cover device holder 51*a* can also be other types of clamps, magnets, adhesives etc.

The air-cleaning device 1 comprises suitably also a second screen cover device holder 51*b*. In some embodiments, where the screen cover device 3 comprises a second unit 23, as shown in FIGS. 1*a* and 1*b*, the second screen cover device holder 51*b* can be similar or identical to the first screen cover device holder 51*a*. In other embodiments of the invention where only a first unit 13 is provided and each screen cover 7 instead is attached in its first end 7*a* to the air cleaning device 1 when this screen cover is to be used as shown in FIGS. 2 and 3 a second screen cover device holder 51*b* can comprise for example hooks as shown in FIG. 2, tape, adhesive, Velcro or magnets or a groove and locking device as shown in FIG. 3.

The first and second screen cover device holders 51*a*, 51*b* are positioned on the air-cleaning device 1 such that a screen cover 7 can be held in a first end 7*a* by either a second unit 23 or the second screen cover device holder 51*b* and in a second end 7*b* by the first unit 13 while the screen cover 7 is covering at least a substantial part of the air outflow area 9 of the screen 11 of the air-cleaning device 1.

In some embodiments of the invention the air-cleaning device 1 further comprises a germicidal radiation source 61 positioned such that the disposable screen cover to be used can be irradiated. The germicidal radiation source 61 can for example comprise a UVC-source, a LED-source, Ionizing radiation source or a pulsating UV-source. The germicidal radiation source 61 can for example be positioned inside the air-cleaning device 1 and a slit 63 can be provided in a casing of the air-cleaning device 1 such that radiation from the germicidal radiation source 61 can escape out. The first screen cover device holder 51*a* can be provided close to this slit 63 such that screen covers 7 will be irradiated by the germicidal radiation source 61 when they are removed from the first unit 13. The first screen cover device holder 51*a* can comprise an enclosing cassette as described above. The enclosing cassette can be designed for not allowing radiation outside which is suitable from a user perspective. The germicidal radiation source 61 can in some embodiments also radiate inwardly into the air-cleaning device 1 such that air to be flowed out through the screen 11 can be irradiated and hereby sterilized. In such an air-cleaning device 1 a HEPA filter may not be necessary or another type of filter may be used.

In another embodiment said germicidal radiation source 61 can be provided to the air-cleaning device 1 such that it can irradiate the disposable screen cover 7 which presently is in use and the air outflow from the air-cleaning device.

In some embodiments of the invention the air-cleaning device 1 further comprises a frame 71 configured to hold the one of the disposable screen covers 7 which is the one to be presently in use in a position such that the disposable screen cover 7 covers at least a substantial part of the air outflow area 9 of the screen 11 of the air-cleaning device 1. The frame 71 comprises in some embodiments one or more pulleys 73 over which the screen covers 7 are running. The frame 71 may also comprise one or more guides 75 which are bent such that the screen cover 7 which is the one presently used is stretched over the guides 75 and provides a curved surface of the screen cover 7. Such guides 75 may be provided one to a top part of the air-cleaning device and one to a bottom part of the air-cleaning device. Hereby the air flow will be guided slightly more towards the sides. Which is advantageous because this will widen the clean zone.

According to the invention an air-cleaning device system comprising an air-cleaning device 1 as described above and a screen cover device 3; 3'; 3" as described above is also provided. The screen cover device 3; 3'; 3" can be connected to the air-cleaning device 1, whereby both the air-cleaning device 1 and the screen cover device 3; 3'; 3" comprises cooperating connecting devices, such as the first and second screen cover device holders 51*a*, 51*b* and the air-cleaning device connector 41 as described above.

The disposable screen covers 7 may comprise a weave from for example nylon, cellulose, mesh or non-woven. One part of the screen covers 7 which will cover the air flow out from the screen 11 of the air-cleaning device 1 should be permeable for the air. The rest of the screen covers 7, which are covering at least parts of side edges 31 of the air cleaning device 1 may be covered by a plastic material.

The invention claimed is:

1. A screen cover device configured for attachment to an air-cleaning device having a screen with an air flow area, wherein said screen cover device comprises:

disposable screen covers each configured, when in use, to cover at least a substantial part of the air outflow area of the screen of the air-cleaning device; and a first unit configured to be mounted to the air-cleaning device and configured for housing the disposable screen covers when the disposable screen covers are not in use, wherein at least two of the disposable screen covers are connected to each other such that they can be removed from the first unit one after the other.

2. A screen cover device according to claim 1, wherein the first unit comprises a roll around which the disposable screen covers are rolled when not in use.

3. A screen cover device according to claim 1, wherein at least one of the disposable screen covers comprises a first end configured for being operably connected to the air-cleaning device and an opposed second end that is held by the first unit when the at least one disposable screen cover is in use covering the air outflow area of the screen of the air-cleaning device.

4. A screen cover device according to claim 1, further comprising:

a second unit for collecting disposable screen covers, which second unit is configured to be mounted to the air-cleaning device such that a disposable screen cover that is presently in use for covering at least a substantial part of the air outflow area of the screen of the air-cleaning device is held between the first and the second units.

5. A screen cover device according to claim 4, wherein the second unit comprises a roll around which one or more of the disposable screen covers can be rolled after the disposable screen covers have been used.

6. A screen cover device according to claim 5, wherein the first unit comprises a roll around which the disposable screen covers are rolled prior to use, and wherein the rolls of the first and second units are configured such that they can be rotated in coordination for unwinding unused disposable screen covers from the roll of the first unit and winding used disposable screen covers onto the roll of the second unit.

7. A screen cover device according to claim 1, wherein the screen cover device is presterilized.

8. A screen cover device for attachment to an air cleaning device having a screen with an air outflow area, said screen cover device comprising:

at least one disposable screen cover; and a first unit configured to be mounted to the air-cleaning device and for keeping the at least one disposable screen cover when not in use, wherein the at least one disposable screen cover is designed to cover at least a substantial part of the air outflow area of the screen of the air-cleaning device and at least parts of side edges of the air-cleaning device, and wherein the screen cover device is configured to be mounted to the air-cleaning device such that the at least one disposable screen cover when in use, covers both at least a substantial part of the air outflow area of the screen of the air-cleaning device and at least parts of side edges of the air-cleaning device.

9. A screen cover device for attachment to an air cleaning device having a screen with an air outflow area, said screen cover device comprising:

at least one disposable screen cover comprising a peelable protective layer; and a first unit configured to be mounted to the air-cleaning device and for keeping the at least one disposable screen cover when not in use.

10. An air-cleaning device comprising:

a screen with an air outflow area where air is flowed out from the air-cleaning device; and a first screen cover device holder configured for holding a first unit, where the first unit is configured for keeping disposable screen covers when the disposable screen covers are not deployed from the first unit in use, wherein the disposable screen covers are each is configured for covering at least a substantial part of the air outflow area of the screen when deployed from the first unit in use, and wherein at least two of the disposable screen covers are connected to each other such that they can be deployed from the first unit one after the other.

11. An air-cleaning device according to claim 10, further comprising a second screen cover device holder for holding a second unit of a screen cover device or for holding a first end of a disposable screen cover deployed from the first unit in use.

12. An air-cleaning device according to claim 11, wherein said second screen cover device holder is positioned such that a disposable screen cover deployed from the first unit in use can be held at a first end either by the second unit or by the second screen cover device holder and at a second end by the first unit while the disposable screen cover deployed from the first unit is covering at least a substantial part of the air outflow area of the screen of the air-cleaning device.

13. An air-cleaning device according to claim 10, further comprising a germicidal radiation source positioned such that the disposable screen covers can be irradiated.

14. An air-cleaning device according to claim 13, wherein said germicidal radiation source is provided such that it can irradiate both: a disposable screen cover deployed from the first unit when in use, and air outflow from the air-cleaning device.

15. An air-cleaning device according to claim 10, further comprising a frame configured to hold one of disposable screen covers when deployed from the first unit in use in a position such that the disposable screen cover deployed from the first unit covers at least a substantial part of the air outflow area of the screen of the air-cleaning device.

16. An air-cleaning device according to claim 15, wherein the frame comprises guides which are bent such that the disposable screen cover, when deployed from the first unit in use, is stretched over the guides and provides a curved surface of the disposable screen cover.

17. An air-cleaning device system comprising:

an air-cleaning device comprising:

a screen with an air outflow area where air is flowed out from the air-cleaning device;

a screen cover device holder; and a screen cover device held by the screen cover device holder and comprising a first unit configured for keeping disposable screen covers when the disposable screen covers are not deployed from the first unit in use, wherein the disposable screen covers are each configured for covering at least a substantial part of the air outflow area of the screen when deployed from the first unit in use, and wherein at least two of the disposable screen covers are connected to each other such that they can be deployed from the first unit one after the other.

* * * * *